(12) United States Patent
Kopito et al.

(10) Patent No.: US 12,426,962 B2
(45) Date of Patent: Sep. 30, 2025

(54) ROBOTIC SURGICAL SYSTEM WITH RIGID BED MOUNT

(71) Applicant: Mazor Robotics Ltd., Caesarea (IL)

(72) Inventors: Dor Kopito, Kibbutz Parod (IL); Ziv Seemann, Beit Ytzhack (IL); Gal Eshed, Atlit (IL); Amir Keret, Atlit (IL); Nimrod Dori, Atlit (IL); Itamar Eshel, Tzur Igal (IL); Yuval Chen, Tel Aviv-Jaffa (IL); Nir Ofer, Tel Aviv-Jaffa (IL); Ori Ben Zeev, Tel Aviv (IL)

(73) Assignee: Mazor Robotics Ltd., Caesarea (IL)

( * ) Notice: Subject to any disclaimer, the term of this patent is extended or adjusted under 35 U.S.C. 154(b) by 652 days.

(21) Appl. No.: 17/351,921

(22) Filed: Jun. 18, 2021

(65) Prior Publication Data
US 2022/0401160 A1  Dec. 22, 2022

(51) Int. Cl.
| | | |
|---|---|---|
| A61B 34/30 | (2016.01) | |
| A61B 6/04 | (2006.01) | |
| A61B 90/50 | (2016.01) | |
| A61B 90/57 | (2016.01) | |
| A61G 13/10 | (2006.01) | |
| B25J 17/02 | (2006.01) | |

(52) U.S. Cl.
CPC .............. *A61B 34/30* (2016.02); *A61B 90/57* (2016.02); *A61G 13/101* (2013.01); *B25J 17/02* (2013.01); *A61B 2090/571* (2016.02)

(58) Field of Classification Search
CPC ... A61B 34/30; A61B 90/57; A61B 2090/571; A61G 13/101; B25J 17/02
See application file for complete search history.

(56) References Cited

U.S. PATENT DOCUMENTS

| | | | |
|---|---|---|---|
| 5,855,583 A | * | 1/1999 | Wang ..................... A61B 34/35 606/139 |
| 6,371,713 B1 | | 4/2002 | Nishimura et al. |
| 9,358,682 B2 | | 6/2016 | Ruiz Morales |
| 2003/0037375 A1 | | 2/2003 | Riley et al. |

(Continued)

FOREIGN PATENT DOCUMENTS

CN        212281683        1/2021

OTHER PUBLICATIONS

"How to Mechatronics, SCARA Robot: How to Build your own Arduino Based Robot, pp. 1-72." (Year: 2020).*

(Continued)

*Primary Examiner* — Benjamin J Klein
*Assistant Examiner* — Thien Jason Tran
(74) *Attorney, Agent, or Firm* — Sheridan Ross P.C.

(57) ABSTRACT

A surgical mount system according to at least one embodiment of the present disclosure includes a bed mount, a tubular base attached to the bed mount and comprising a telescoping member slidably coupled with the tubular base, the telescoping member comprising a first end and a second end, wherein the first end is disposed inside the tubular base, and wherein the telescoping member translates linearly along an axis of the tubular base; and a support arm attached to the second end of the telescoping member, the support arm having a length running from a proximal end to a distal end, wherein the support arm rotates relative to the bed mount about the axis of the tubular base.

20 Claims, 5 Drawing Sheets

(56) References Cited

U.S. PATENT DOCUMENTS

| | | | |
|---|---|---|---|
| 2012/0071895 A1* | 3/2012 | Stahler | A61B 34/20 |
| | | | 606/130 |
| 2018/0078439 A1* | 3/2018 | Cagle | A61B 34/70 |
| 2020/0110936 A1* | 4/2020 | Hares | A61B 1/3132 |
| 2021/0030496 A1* | 2/2021 | Devengenzo | A61B 34/30 |
| 2021/0045626 A1 | 2/2021 | Hsu et al. | |

OTHER PUBLICATIONS

International Search Report and Written Opinion for International (PCT) Patent Application No. PCT/IL2022/050632, dated Sep. 30, 2022, 15 pages.

How to Mechatronics "SCARA Robot | How to Build Your Own Arduino Based Robot," YouTube, Oct. 2, 2020, 72 pages [retrieved online from: www.youtube.com/watch?v=1QHJksTrk8s].

* cited by examiner

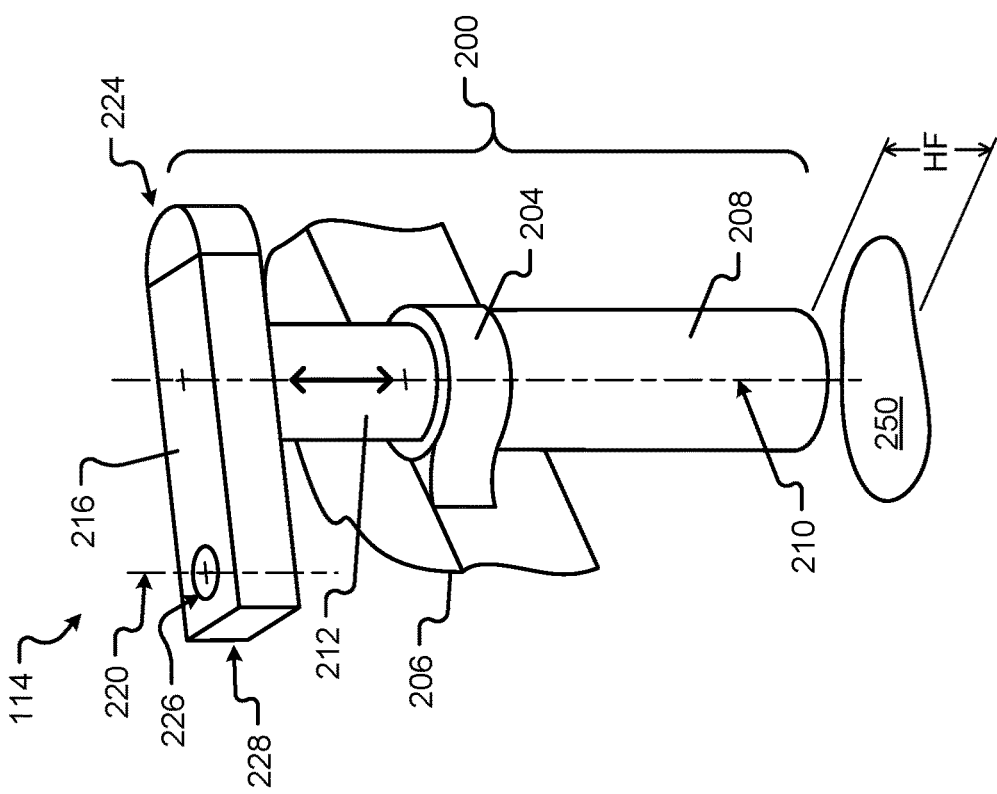
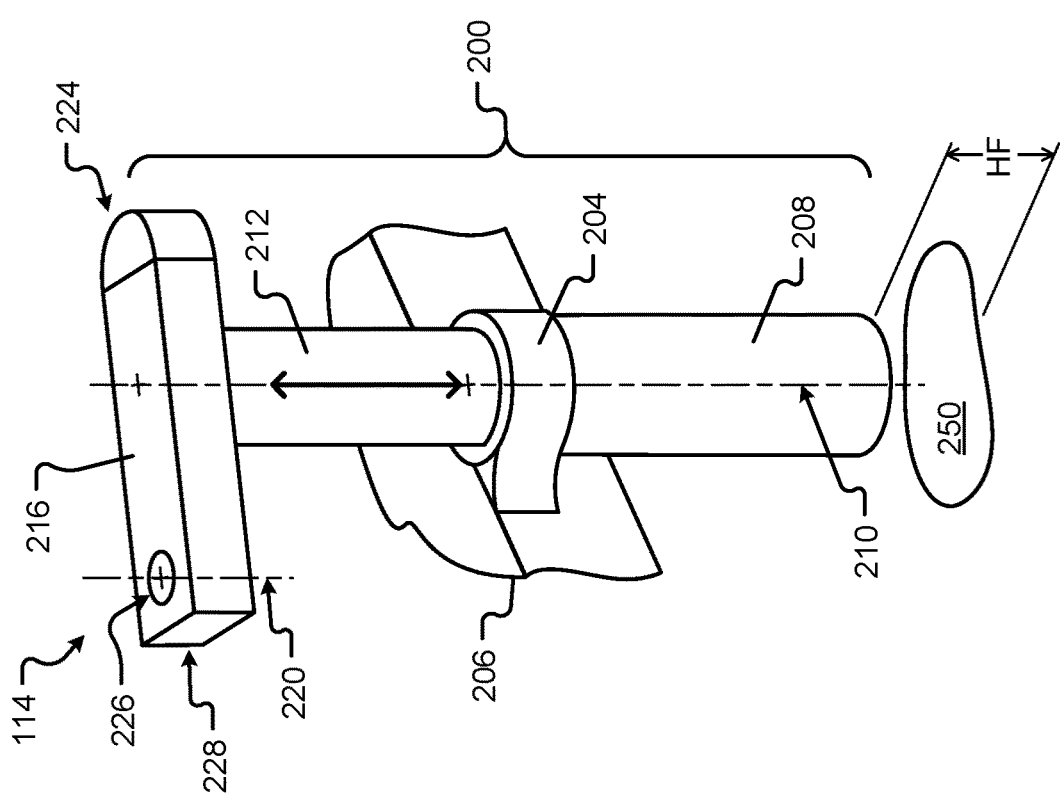

ROBOTIC SURGICAL SYSTEM WITH RIGID BED MOUNT

FIELD

The present disclosure is generally directed to surgical systems, and relates more particularly to robotic surgical devices.

BACKGROUND

Surgical robots may assist a surgeon or other medical provider in carrying out a surgical procedure, or may complete one or more surgical procedures autonomously. Providing controllable linked articulating members allows a surgical robot to reach areas of a patient anatomy during various medical procedures.

SUMMARY

Example aspects of the present disclosure include:

A system according to at least one embodiment of the present disclosure comprises: a bed mount, a tubular base attached to the bed mount and comprising a telescoping member slidably coupled with the tubular base, the telescoping member comprising a first end and a second end, wherein the first end is disposed inside the tubular base, and wherein the telescoping member translates linearly along an axis of the tubular base; and a support arm attached to the second end of the telescoping member, the support arm having a length running from a proximal end to a distal end, wherein the support arm rotates relative to the bed mount about the axis of the tubular base.

Any of the aspects herein, wherein the bed mount comprises a fixed and completely constrained interface between the tubular base and a surgical bed.

Any of the aspects herein, wherein the support arm further comprises a surgical arm mount disposed at the distal end of the support arm, and wherein the surgical arm mount provides a revolute joint interface between the support arm and a surgical arm.

Any of the aspects herein, further comprising: a first degree of freedom between the bed mount and the telescoping member corresponding to a linear translational degree of freedom of the system; and a second degree of freedom between the support arm and the bed mount corresponding to a rotational degree of freedom of the system, wherein the system comprises only two degrees of freedom from the bed mount to the tubular base, from the tubular base to the telescoping member, and from the telescoping member to the support arm, the two degrees of freedom corresponding to the first degree of freedom and the second degree of freedom.

Any of the aspects herein, wherein the support arm comprises a prismatic joint that provides linear translation of the distal end of the support arm relative to the axis of the tubular base.

Any of the aspects herein, wherein the telescoping member rotates relative to the tubular base allowing the support arm to rotate relative to the bed mount about the axis of the tubular base.

Any of the aspects herein, wherein the telescoping member is rotationally fixed relative to the tubular base and a rotational degree of freedom is disposed between the support arm and the second end of the telescoping member allowing the support arm to rotate relative to the bed mount and the telescoping member about the axis of the tubular base.

Any of the aspects herein, wherein at least one of the tubular base and the telescoping member is circular in cross-section, and wherein an axis of the telescoping member coincides with the axis of the tubular base.

A robotic system according to at least one embodiment of the present disclosure comprises: a surgical bed comprising a rigid frame configured to position a patient at a height offset from a floor; a bed mount fixedly attached to the rigid frame of the surgical bed; a tubular base attached to the bed mount and comprising a telescoping member slidably coupled with the tubular base, the telescoping member comprising a first end and a second end, wherein the first end is disposed inside the tubular base, and wherein the telescoping member translates linearly along an axis of the tubular base; and a support arm attached to the second end of the telescoping member, the support arm having a length running from a proximal end to a distal end, wherein the support arm rotates relative to the bed mount about the axis of the tubular base, wherein the tubular base, the telescoping member, and the support arm are supported by the bed mount, and wherein no portion of the tubular base, the telescoping member, and the support arm contact the floor.

Any of the aspects herein, wherein the tubular base is offset from the floor a clearance height that is maintained during operation of the robotic system.

Any of the aspects herein, wherein a majority of the tubular base is arranged in a space disposed between an operating table surface of the surgical bed and the floor.

Any of the aspects herein, further comprising: a surgical arm attached to the distal end of the support arm, wherein the surgical arm is attached at a revolute joint disposed between the support arm and the surgical arm, and wherein the surgical arm comprises a robotic mechanism having at least five degrees of freedom.

Any of the aspects herein, further comprising: a first degree of freedom between the bed mount and the telescoping member corresponding to a linear translational degree of freedom of the robotic system; and a second degree of freedom between the support arm and the bed mount corresponding to a rotational degree of freedom of the robotic system, wherein the robotic system comprises only two degrees of freedom from the bed mount to the tubular base, from the tubular base to the telescoping member, and from the telescoping member to the support arm, the two degrees of freedom corresponding to the first degree of freedom and the second degree of freedom Any of the aspects herein, wherein the support arm comprises a prismatic joint that provides linear translation of the distal end of the support arm relative to the axis of the tubular base.

Any of the aspects herein, wherein the telescoping member rotates relative to the tubular base allowing the support arm to rotate relative to the bed mount about the axis of the tubular base.

Any of the aspects herein, wherein the telescoping member is rotationally fixed relative to the tubular base and a rotational degree of freedom is disposed between the support arm and the second end of the telescoping member allowing the support arm to rotate relative to the bed mount and the telescoping member about the axis of the tubular base.

Any of the aspects herein, wherein at least one of the tubular base and the telescoping member is polygonal in cross-section, and wherein an axis of the telescoping member coincides with the axis of the tubular base.

A robotic system according to at least one embodiment of the present disclosure comprises: a bed mount bracket; a column attached to the bed mount bracket, the column configured to linearly translate along an axis of the column relative to the bed mount bracket providing a first degree of freedom for the robotic system; a support arm attached to the column, the support arm extending a length from a first point to a second point, the support arm disposed perpendicular to the column; and a revolute joint disposed between the support arm and the bed mount bracket, the revolute joint configured to provide rotation of the support arm about the axis of the column, the revolute joint providing a second degree of freedom for the robotic system.

Any of the aspects herein, wherein the revolute joint is disposed between the column and the support arm.

Any of the aspects herein, wherein the robotic system comprises a total of only two degrees of freedom running from the bed mount bracket to the column and then from the column to the support arm, the two degrees of freedom corresponding to the first degree of freedom and the second degree of freedom for the robotic system.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 2B is a diagram of a surgical mount system in a first extended state according to at least one embodiment of the present disclosure;

FIG. 2C is a diagram of a surgical mount system in a first retracted state according to at least one embodiment of the present disclosure;

DETAILED DESCRIPTION

Figure 1:
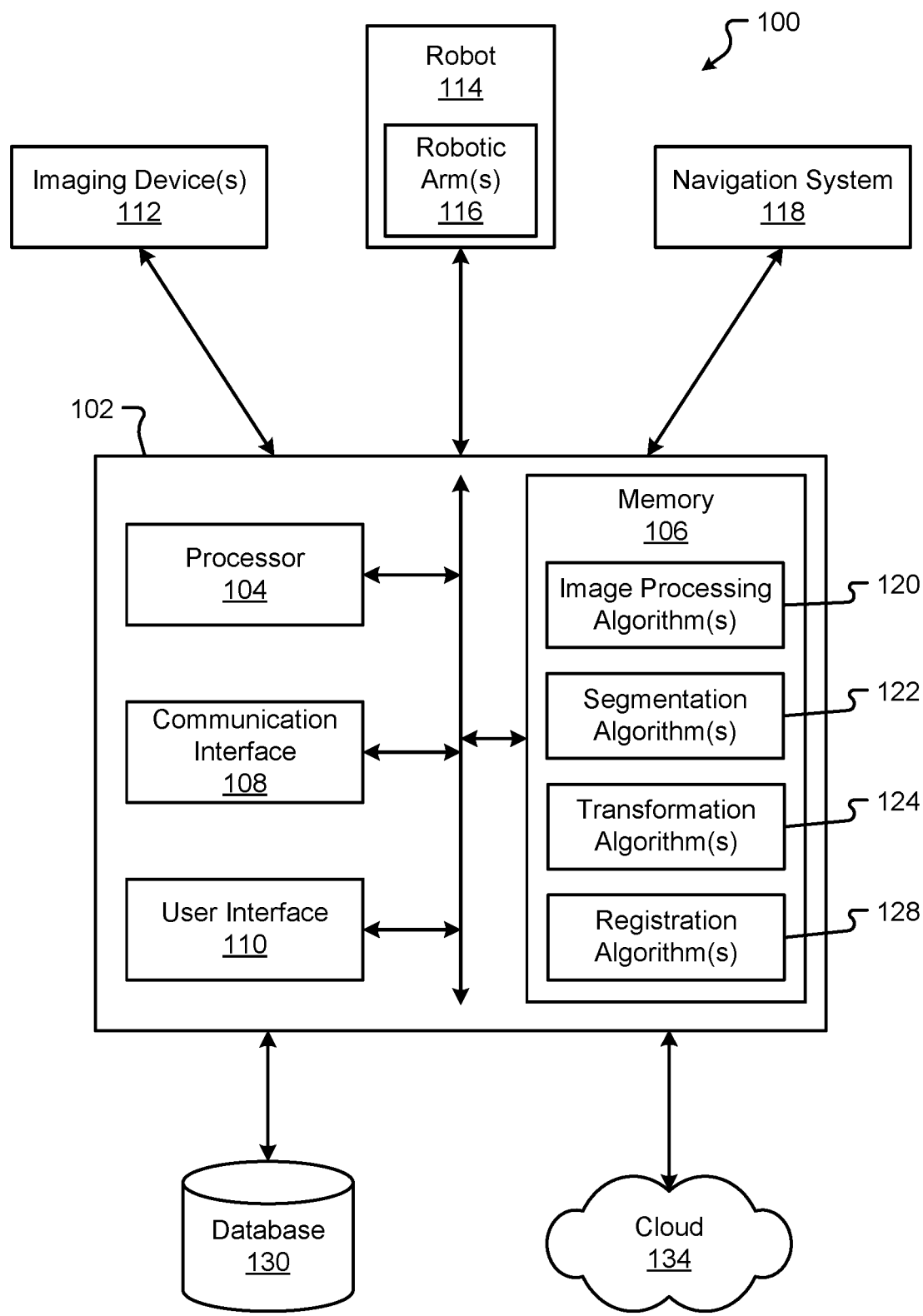
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Mounting a robotic system, especially a robotic surgical system, to a surgical bed or operating table allows to improve accuracy and enhance clearance around the operating area of a patient. However, since the robotic system may be mounted to the bed, the weight of the system and interfaces must be specific to bed-mounted interfaces. Traditionally, at least four degrees of freedom (e.g., located along the Z-axis, Y-axis, first revolute joint rotation, second revolute joint rotation) are required before a surgical arm can be mounted to the robotic system. These degrees of freedom were relied upon to locate the surgical arm above the patient in order to connect it to the patient during surgery set up (e.g., performing a "bone mount," etc.). Not only does this traditional approach limit possibilities to add other features, but the design is not spatially optimized (e.g., there are four degrees of freedom required to locate the arm at a three degree of freedom position).

It is an aspect of the present disclosure to optimize a surgical mount system by reducing the overall weight of the robotic system, decreasing the number of required degrees of freedom, and providing a rigid and stable interface for mounting to a bed and/or operating table (e.g., off or physically separated from the floor, wall, ceiling, etc.). In one embodiment, the surgical mount system may employ a tubular linear and rotational degree of freedom that can move up/down and rotate. In some embodiments, only one rotational degree of freedom may be required for the surgical mount system. A surgical arm may then be attached to a mount point of the surgical mount system providing enhanced movement capabilities for surgical procedures.

In one embodiment, the surgical mount system having fewer degrees of freedom may provide fewer mechanisms, less weight, decreased complexity, higher rigidity (e.g., better and more accurate registration), and a more economical surgical mount system than other (e.g., conventional) designs. In some embodiments, a main support or upright may be tubular (e.g., of any cross-section) and optimized for rigidity and stiffness. As a result, the overall accuracy of the surgical mount system is enhanced compared to conventional designs. Another benefit of the surgical mount system having fewer links and degrees of freedom (e.g., fewer links and movement axes) includes, but is in no way limited to, providing an increased working area for a surgeon, medical assistant, nurse, or other individual positioned around the bed or operating table.

A surgical mount system according to at least one embodiment of the disclosure comprises: a bed-mounted tubular base having a first linear translation degree of freedom running along a first direction defining a first axis and a first rotational degree of freedom around the first axis, a link arm attached to a translational end of the base, the link arm comprising a surgical arm mount point disposed a distance from the tubular base, the surgical arm mount point defining a second axis and a second rotational degree of freedom for a surgical arm. Aspects include wherein the link arm comprises a second linear translational degree of freedom running along a second direction extending perpendicularly from the direction such that the surgical arm mount point is movable linearly relative to the tubular base.

Among other things, the surgical mount system reduces a number of links, joints, and related degrees of freedom than may be associated with traditional surgical systems. In some embodiments, the present disclosure provides a lighter weight system to be produced having fewer parts than are found in conventional designs. As the degrees of freedom of the system are reduced so is the inertia of the system, which allows for smaller, more energy efficient, motors to be used to move the remaining links/joints. Moreover, reducing the number of components in the design increases the overall rigidity of the system while providing enhanced clearance around the patient. Utilizing fewer links/joints than may be found in conventional systems provides a lighter weight mount system that has better bed-mounting capability, providing clearance under the system, and resulting in a cleaner surgical system.

Embodiments of the present disclosure provide technical solutions to one or more of the problems of (1) heavy robotic systems fixedly mounted to building structures (e.g., the floor, ceiling, wall, etc.) that provide decreased accuracy (e.g., by being located further from a patient), higher complexity (e.g., having a greater number of links and/or degrees of freedom between the mount point and the surgical arm, etc.), and crowded workspaces (e.g., taking up valuable space near a bed or operating table), (2) setting up and arranging a surgical arm on the end of a surgical mount system that has multiple degrees of freedom and the increased variability associated therewith relative to a patient on a surgical bed or operating table, (3) failing to be able to mount to a bed, off the floor, where a patient is located and providing close stable robotic interface for mounting a surgical arm, and (4) providing a clean robotic system that is not mounted to dirty or unsterile surfaces such as floors, walls, or ceilings of an operating theater, etc.

Turning first to FIG. 1, a block diagram of a system 100 according to at least one embodiment of the present disclosure is shown. The system 100 may be used to control, pose, and/or otherwise manipulate a surgical mount system, a surgical arm, and/or surgical tools attached thereto and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods described herein, or of any other methods. The memory 106 may store, for example, one or more image processing algorithms 120, one or more segmentation algorithms 122, one or more transformation algorithms 124, and/or one or more registration algorithms 128. Such instructions or algorithms may, in some embodiments, be organized into one or more applications, modules, packages, layers, or engines. Alternatively or additionally, the memory 106 may store other types of data (e.g., machine learning modes, artificial neural networks, etc.) that can be processed by the processor 104 to carry out the various method and features described herein. Thus, although various components of memory 106 are described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The system 100 or similar systems may be used, for example, to carry out one or more aspects of any of the methods described herein. The system 100 or similar systems may also be used for other purposes.

Referring now to FIGS. 2A-2E, diagrams of the robotic surgical system 100 and the components thereof are shown according to at least one embodiment of the present disclosure. In some embodiments, the robot 114 may comprise a surgical mount system 200 and a robotic arm 116. The robotic arm 116 may correspond to a surgical arm as described above. In one embodiment, the surgical arm may correspond to a six-axis surgical robot or surgical robotic system such as the Mazor X™ Stealth Edition robotic guidance system. In one embodiment, the surgical mount system 200 may provide a rigid, limited degree of freedom, surgical mount system to which the robotic arm 116 may be mounted.

Figure 2A:
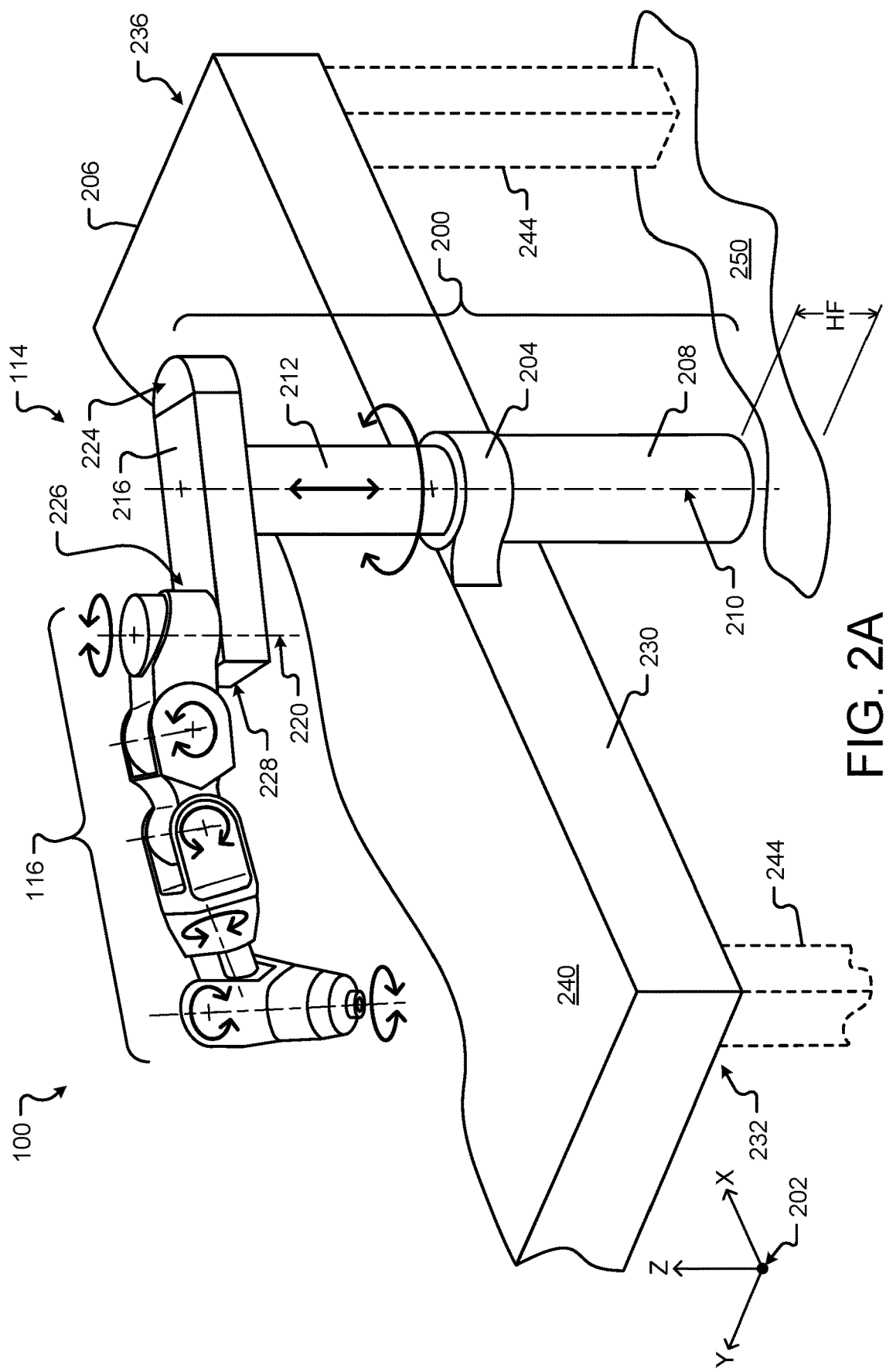
FIG. 2A is a diagram of a robotic surgical system according to at least one embodiment of the present disclosure.

Features of the robot 114 and/or system 100 may be described in conjunction with a coordinate system 202. The coordinate system 202, as shown in FIG. 2A, includes three-dimensions comprising an X-axis, a Y-axis, and a Z-axis. Additionally or alternatively, the coordinate system 202 may be used to define planes (e.g., the XY-plane, the XZ-plane, and the YZ-plane) of the robot 114 and/or system 100. These planes may be disposed orthogonal, or at 90 degrees, to one another. While the origin of the coordinate system 202 may be placed at any point on or near the components of the robot 114, for the purposes of description, the axes of the coordinate system 202 are always disposed along the same directions from figure to figure, whether the coordinate system 202 is shown or not. In some examples, reference may be made to dimensions, angles, directions, relative positions, and/or movements associated with one or more components of the robot 114 and/or system 100 with respect to the coordinate system 202. For example, the width of the surgical bed 206 (e.g., running from the first side 232 to the second side 236) may be defined as a dimension along the X-axis of the coordinate system 202, the height of the surgical bed 206 may be defined as a dimension along the Z-axis of the coordinate system 202, and the length of the surgical bed 206 may be defined as a dimension along the Y-axis of the coordinate system 202. Additionally or alternatively, the height of the surgical mount system 200 may be defined as a dimension along the Z-axis of the coordinate system 202, a reach of the surgical mount system 200 may be defined as a dimension along the Y-axis of the coordinate system 202, and a working area of the surgical mount system 200 may be defined in the XY-plane with reference to the corresponding axes of the coordinate system 202.

The surgical mount system 200 may comprise a bed mount bracket 204, a tubular base 208, a telescoping member 212, and a support arm 216. It is an aspect of the present disclosure that the surgical mount system 200 mounts to a surgical bed 206 (e.g., via the bed mount bracket 204). As illustrated in FIG. 2A, the surgical bed 206 may comprise at least one operating table surface 240, mount surface 230, and legs 244 or supports. One or more of the various surfaces 230, 240 and/or the legs 244 may make up the frame of the surgical bed 206. In any event, the surgical bed comprising may be configured to position a patient at a height offset from the floor 250. For instance, a patient may lie on the operating table surface 240 of the surgical bed 206.

The bed mount bracket 204 may comprise a bracket, clamp, plate, or other structure that attaches to the mount surface 230 of the surgical bed 206. In one embodiment, the bed mount bracket 204 may be fastened to the mount surface 230 using one or more screws or bolts. In some embodiments, the bed mount bracket 204 may be welded, adhered, or otherwise affixed to the surgical bed 206. In any event, the bed mount bracket 204, once attached to the mount surface 230 will remain immovable relative to any side 232, 236 or surface 230, 240 of the surgical bed 206. Stated another way, the bed mount bracket 204 may provide a completely constrained interface (e.g. having no degrees of freedom of movement) relative to the surgical bed 206.

The surgical mount system 200 may comprise a first linear translation joint disposed between the bed mount bracket 204 and the support arm 216. This first linear translation joint may correspond to a prismatic joint, one or more telescoping tubular members, a movable column, an extendable/retractable rod, and/or any other linearly actuated member. In one embodiment, the first linear translation joint may comprise a tubular base 208 mounted or otherwise affixed to the bed mount bracket 204 and a telescoping member 212 that translates linearly along a tubular base axis 210 relative to the tubular base 208 and/or the bed mount bracket 204. In some embodiments, the tubular base axis 210 may be colinear with an axis of the telescoping member 212. At least one of the tubular base 208 and the telescoping member 212 may have a polygonal cross-section of any shape. Examples of the polygonal cross-sectional shape may include, but are in no way limited to, rectangular, square, pentagonal, hexagonal, octagonal, oval, circular, etc., and/or combinations thereof.

In one embodiment, a linear actuator (e.g., screw actuator, etc.) may be embedded in a portion of the tubular base 208 and/or the telescoping member 212 and configured to provide the linear movement of the telescoping member 212 relative to the tubular base 208 (e.g., along the Z-axis). The telescoping member 212 may have a first end disposed inside a body of the tubular base 208 and a second end disposed opposite the first end. The second end of the telescoping member 212 may be attached to the support arm 216.

As described herein, the surgical mount system 200 may comprise a linear translational degree of freedom (e.g., provided by the tubular base 208 and the telescoping member 212) and a rotational degree of freedom that allows the support arm 216 to rotate (e.g., in the XY-plane) relative to the bed mount bracket 204.

In one embodiment, the surgical mount system 200 may comprise a revolute joint disposed between the telescoping member 212 and the support arm 216 allowing the support arm 216 to rotate relative to the bed mount and relative to the telescoping member about the tubular base axis 210. In this case, the telescoping member 212 may be rotationally fixed relative to the tubular base 208 and the only rotational degree of freedom between the support arm 216 and the bed mount bracket 204 may be located at the interface between the telescoping member 212 and the support arm 216.

Alternatively, the surgical mount system 200 may comprise a revolute joint disposed between the tubular base 208 and the telescoping member 212. In this embodiment, the support arm 216 may be rotationally fixed relative to the telescoping member 212 and when the telescoping member 212 rotates relative to the tubular base 208 (e.g., about the tubular base axis 210) the support arm 216 rotates with the telescoping member 212. When the telescoping member 212 rotates, the support arm 216 rotates relative to the bed mount bracket 204 about tubular base axis 210.

The rotational degrees of freedom and/or revolute joints, as described herein, may comprise a gear motor, stepper motor, servo motor, and/or some other rotationally controlled and actuated joint or coupling.

Providing a limited number of degrees of freedom between the bed mount bracket 204 and the support arm 216 allows the surgical mount system 200 to provide a rigid interface and mount for the robotic arm 116 (e.g., the surgical arm). The support arm 216 may be disposed orthogonal or perpendicular to the tubular base axis 210. In some embodiments, the support arm 216 has a length running from a proximal end 224 to a distal end 228 thereof. The robotic arm 116 may mount to the support arm 216 at the surgical arm mount 226 disposed adjacent to the distal end 228. The support arm 216 may provide a beam or other member that extends outwardly from the telescoping member 212 in a direction away from the tubular base axis 210 (e.g., in the XY-plane). This cantilever structure provides a rigid support to which the robotic arm 116 may attach. In some embodiments, the surgical arm mount 226 may comprise a revolute joint or revolute joint mount that provides a first rotational degree of freedom for the robotic arm 116.

In one embodiment, the surgical mount system 200 may comprise a total of only two degrees of freedom between the bed mount bracket 204 and the support arm 216. These two degrees of freedom may correspond to the linear degree of freedom between the tubular base 208 and telescoping member 212 (e.g., shown as the linear arrows disposed on the tubular base axis 210 of FIG. 2A) and the rotational degree of freedom between the tubular base 208 and the support arm 216 (e.g., shown as the rotational arrows adjacent to the bed mount bracket 204 in FIG. 2A).

The support arm 216, or a portion thereof, may be movable, translatable, or extendable in a linear direction (e.g., along a line running from the proximal end 224 to the distal end 228). In one embodiment, the support arm 216 may comprise a prismatic joint that provides linear translation of the distal end 228 of the support arm 216 relative to the tubular base axis 210 (e.g., measured in the XY-plane). In some embodiments, the entire support arm 216 may move relative to the tubular base axis 210. For instance, the telescoping member 212 may comprise a carriage disposed at the second end thereof and the support arm 216 may comprise one or more rails that interface with the carriage. When actuated, a linear actuator (e.g., screw, cylinder, pulley system, etc.) may move the support arm 216 and rails along the carriage to change the distance between the surgical arm rotation axis 220 and the tubular base axis 210.

It is an aspect of the present disclosure that the surgical mount system 200 can be entirely supported by the bed mount bracket 204 attached to the surgical bed 206. As shown in FIG. 2A, no portion of the tubular base 208, the telescoping member 212, and/or the support arm 216 contact the floor 250. Rather, a height-to-floor clearance, HF, is shown between the tubular base 208 and the floor 250. This height-to-floor clearance, HF, ensures that no part of the surgical mount system 200 contacts the floor 250 of an operating theater. As such, the cleanliness of the surgical mount system 200 can be guaranteed and maintained during operation, storage, and/or the like. Moreover, the height-to-floor clearance, HF, provides operators, surgeons, and medical staff with access in and around the surgical bed 206 and patient.

Mounting the tubular base 208 of the surgical mount system 200 beneath the operating table surface 240, but above and offset from the floor 250, provides additional advantages. For example, the weight of the surgical mount system 200 may be predominantly in the tubular base 208 and, as such, the center of gravity of the surgical mount system 200 is lowered when compared to a system that is mounted to the operating table surface 240 of the surgical bed 206. As such, the surgical mount system 200 is balanced about the operating table surface 240 and the stresses on the bed mount bracket 204 due to bending and/or the like is dramatically reduced.

FIGS. 2B and 2C show block diagrams of the surgical mount system 200 in first linear translation states (along the Z-axis) in accordance with embodiments of the present disclosure. For the sake of clarity in disclosure, the robotic arm 116 has been omitted from the views shown in FIGS. 2B and 2C.

In FIG. 2B, the surgical mount system 200 is shown in a first extended state according to at least one embodiment of the present disclosure. In some embodiments, the telescoping member 212 may be actuated to move the support arm 216 to a position further from the bed mount bracket 204 in the Z-axis. In FIG. 2B, the surgical mount system 200 is shown in a first retracted state according to at least one embodiment of the present disclosure. When retracted, the telescoping member 212 may further enter the body of the tubular base 208 bringing the support arm 216 closer to the bed mount bracket 204. It should be appreciated that the telescoping member 212 and the support arm 216 may be moved to any height along the Z-axis that is supported by the tubular base 208 and the surgical mount system 200 via the linear translation described herein.

Figure 2D:
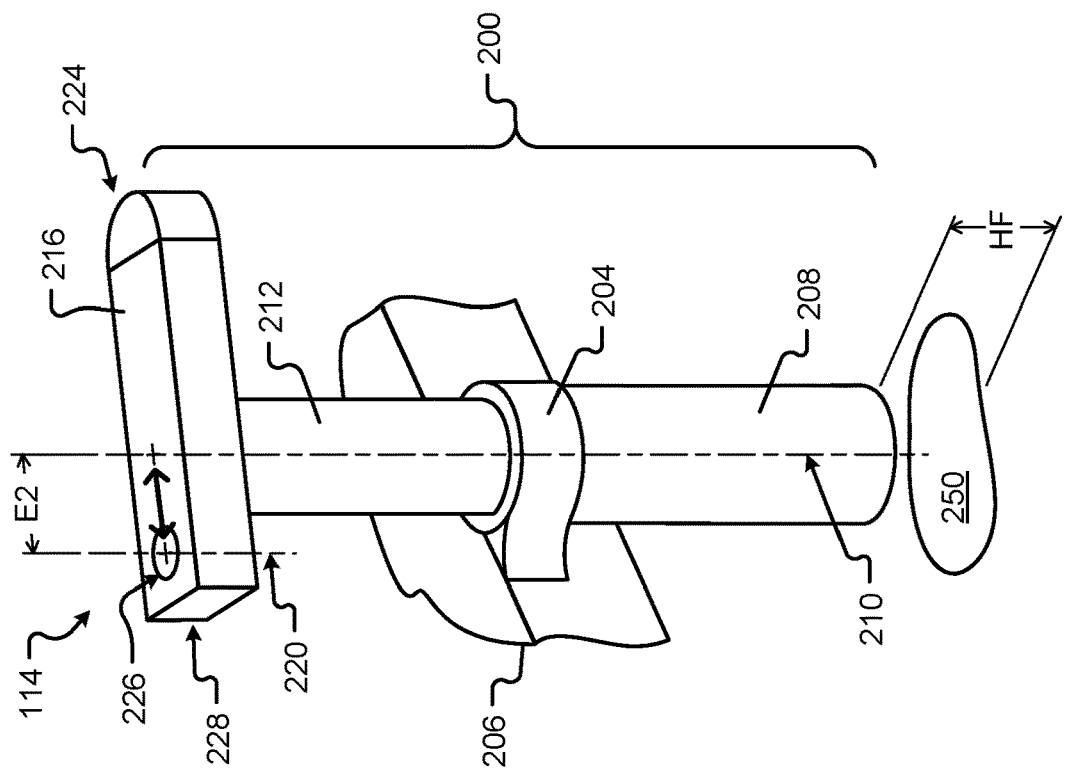
FIG. 2D is a diagram of a surgical mount system in a second extended state according to at least one embodiment of the present disclosure.
Figure 2E:
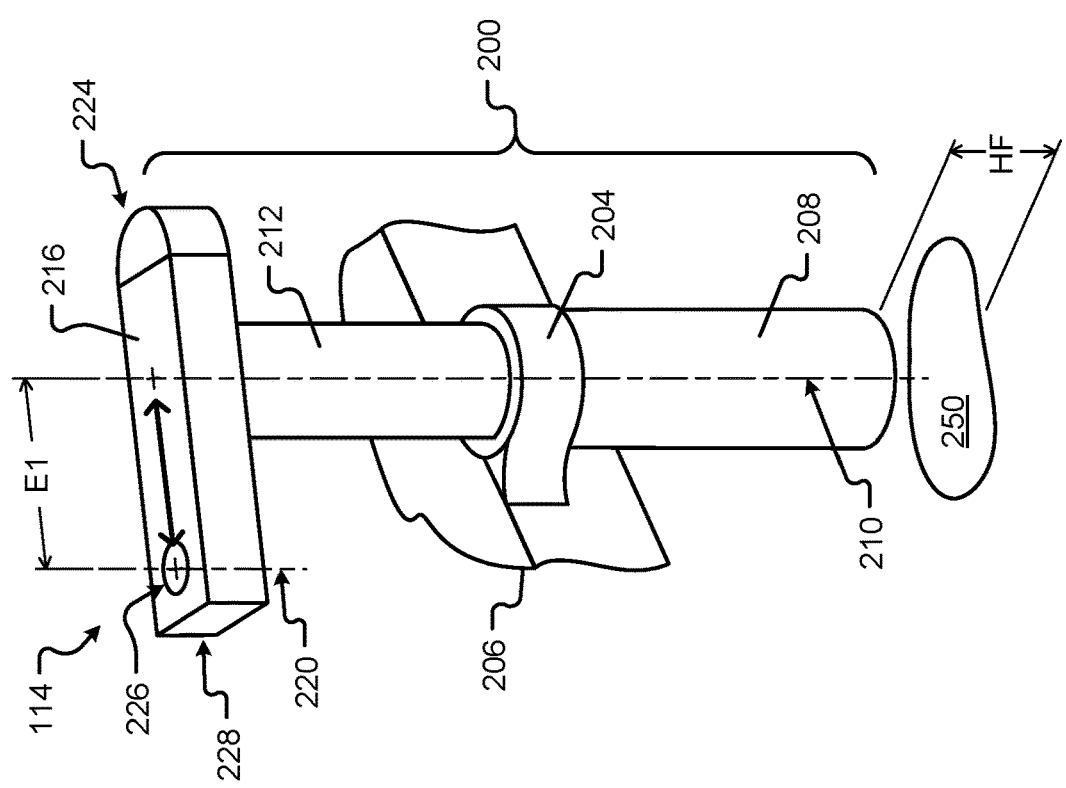
FIG. 2E is a diagram of a surgical mount system in a second retracted state according to at least one embodiment of the present disclosure.

FIGS. 2D and 2E show block diagrams of the surgical mount system 200 in second linear translation states (in the XY-plane) in accordance with embodiments of the present disclosure. For the sake of clarity in disclosure, the robotic arm 116 has been omitted from the views shown in FIGS. 2D and 2E.

In FIG. 2D, the support arm 216 is shown in a second extended state according to at least one embodiment of the present disclosure. In the second extended state, the surgical arm rotation axis 220 (e.g., providing the axis of rotation for the surgical arm mount 226) is shown disposed a first extension distance, E1, from the tubular base axis 210. In FIG. 2E, illustrating a second retracted state, the surgical arm rotation axis 220 (e.g., providing the axis of rotation for the surgical arm mount 226) is shown disposed a second extension distance, E2, from the tubular base axis 210. As illustrated in FIGS. 2D and 2E, the first extension distance, E1, is greater than the second extension distance, E2. It should be appreciated that the surgical arm rotation axis 220 of the support arm 216 may be moved to any extension distance in the XY-plane that is supported by the linear translation of the support arm 216 described herein.

Figure 3:
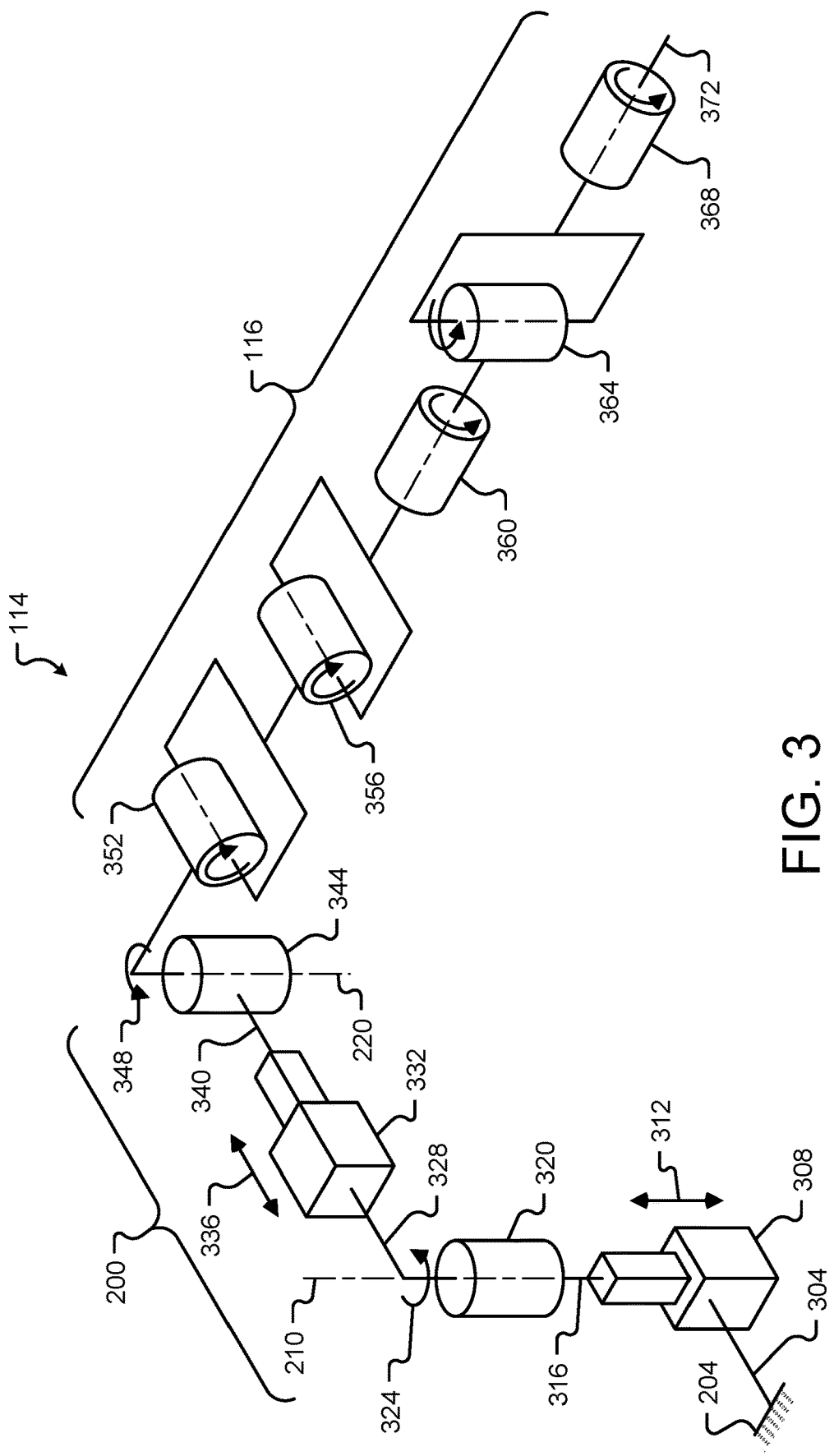
FIG. 3 is a schematic kinematic diagram of a robotic surgical system according to at least one embodiment of the present disclosure.

Referring to FIG. 3, a schematic kinematic block diagram of a robotic surgical system 114 is shown according to at least one embodiment of the present disclosure. As provided above, the robot 114 may comprise a surgical mount system 200 and a robotic arm 116 attached to the surgical mount system 200. The surgical mount system 200 may be attached to a surgical bed 206 and provide a rigid, but lightweight, support system for the robotic arm 116 to be positioned and mounted to.

The surgical mount system 200 shown in FIG. 3 comprises a bed mount bracket 204 and a first link 304 joining the first prismatic joint 308 to the bed mount bracket 204. The first prismatic joint 308 may comprise any linear translation joint that is configured to provide a first linear translational degree of freedom 312 for the surgical mount system 200. In some embodiments, the first prismatic joint 308 may correspond to one or more components of the tubular base 208 and telescoping member 212 described in conjunction with FIGS. 2A-2E. A second link 316 is connected to a translating portion of the first prismatic joint 308 and a first revolute joint 320 is connected to the second link 316. The first revolute joint 320 may provide a first rotational degree of freedom 324 about the tubular base axis 210 for the support arm 216 of the surgical mount system 200. The third link 328 may be attached to the first revolute joint 320.

In one embodiment, the support arm 216 may optionally provide an additional linear translational degree of freedom 336. For instance, the support arm 216 may adjust in the XY-plane to move a surgical arm rotation axis 220 relative to the tubular base axis 210 of the surgical mount system 200. In some embodiments, this linear movement may be made while the tubular base axis 210 and the surgical arm rotation axis 220 remain parallel to one another. The second prismatic joint 332 may provide this second linear translational degree of freedom 336. In some embodiments, the second prismatic joint 332 may be the same as, or similar to, the first prismatic joint 308. In one embodiment, the second prismatic joint 332 may correspond to the rail and carriage description provided in conjunction with FIGS. 2A-2E above.

In some embodiments, the third link 328 and the fourth link 340 may form the support arm 216 without the second prismatic joint 332 and the associated second linear translational degree of freedom 336.

The fourth link 340 may connect with a second revolute joint 344 disposed at a distal end 228 of the support arm 216. The second revolute joint 344 may provide a second rotational degree of freedom 348. In one embodiment, the second revolute joint 344 may be a part of the surgical mount system 200. Additionally or alternatively, the second revolute joint 344 may be a part of the robotic arm 116. In any event, the second rotational degree of freedom 348 may be provided about the surgical arm rotation axis 220 of the surgical mount system 200 and surgical arm mount 226.

The robotic arm 116 may comprise a number of revolute joints 344, 352, 356, 360, 364, 368 and may be connected to the surgical mount system 200 at the surgical arm mount 226. In some embodiments, the robotic arm 116 may correspond to a surgical arm comprising a robotic mechanism having at least five degrees of freedom. The robotic arm 116 may be connected to the second revolute joint 344 and/or the fourth link 340 of the surgical mount system 200. In some embodiments, the robotic arm 116 may comprise the second revolute joint 344, third revolute joint 352, fourth revolute joint 356, fifth revolute joint 360, sixth revolute joint 364, and seventh revolute joint 368 comprising a six-axis robotic system along with respective and associated degrees of freedom. An end effector link 372 may be disposed at the end of the seventh revolute joint 368 and may comprise a receptacle, mount, gripper, or other interface for interacting with a surgical instrument or tool.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system, comprising:
a bed mount attached to a surgical bed adjacent an operating table surface of the surgical bed;
a tubular base extending from an upper end of the tubular base to a lower end of the tubular base, the tubular base fixedly attached to the bed mount at the upper end of the tubular base, wherein the upper end of the tubular base is arranged adjacent the operating table surface of the surgical bed, wherein the lower end of the tubular base is arranged beneath the operating table surface of the surgical bed and offset a clearance height from a floor, wherein the tubular base comprises a telescoping member slidably coupled with the tubular base, the telescoping member comprising a first end and a second end, wherein the first end is disposed inside the tubular base, and wherein the telescoping member translates linearly along an axis of the tubular base; and
a support arm attached to the second end of the telescoping member, the support arm having a length running from a proximal end to a distal end, wherein the support arm rotates relative to the bed mount about the axis of the tubular base, and wherein the telescoping member rotates relative to the tubular base allowing the support arm to rotate relative to the bed mount about the axis of the tubular base.

2. The system of claim 1, wherein the bed mount comprises a fixed and completely constrained interface between the tubular base and a surgical bed.

3. The system of claim 2, wherein the support arm further comprises a surgical arm mount disposed at the distal end of the support arm, and wherein the surgical arm mount provides a revolute joint interface between the support arm and a surgical arm.

4. The system of claim 2, further comprising:
a first degree of freedom between the bed mount and the telescoping member corresponding to a linear translational degree of freedom of the system; and
a second degree of freedom between the support arm and the bed mount corresponding to a rotational degree of freedom of the system,
wherein the system comprises a total of two degrees of freedom between the bed mount and the support arm, the two degrees of freedom comprising only the first degree of freedom and the second degree of freedom.

5. The system of claim 1, wherein the support arm comprises a prismatic joint that provides linear translation of the distal end of the support arm relative to the axis of the tubular base.

6. The system of claim 1, wherein the telescoping member is rotationally fixed relative to the tubular base and a rotational degree of freedom is disposed between the support arm and the second end of the telescoping member allowing the support arm to rotate relative to the bed mount and the telescoping member about the axis of the tubular base.

7. The system of claim 1, wherein at least one of the tubular base and the telescoping member is circular in cross-section, and wherein an axis of the telescoping member coincides with the axis of the tubular base.

8. A robotic system, comprising:
a surgical bed comprising a rigid frame configured to position a patient at a height offset from a floor;
a bed mount fixedly attached to the rigid frame of the surgical bed adjacent an operating table surface of the surgical bed;
a tubular base extending from an upper end of the tubular base to a lower end of the tubular base, the tubular base fixedly attached to the bed mount at the upper end of the tubular base, wherein the upper end of the tubular base is arranged adjacent the operating table surface of the surgical bed, wherein the lower end of the tubular base is arranged beneath the operating table surface of the surgical bed and offset a clearance height from a floor, wherein the tubular base comprises a telescoping member slidably coupled with the tubular base, the telescoping member comprising a first end and a second end, wherein the first end is disposed inside the tubular base, and wherein the telescoping member translates linearly along an axis of the tubular base; and
a support arm attached to the second end of the telescoping member, the support arm having a length running from a proximal end to a distal end, wherein the support arm rotates relative to the bed mount about the axis of the tubular base,
wherein the tubular base, the telescoping member, and the support arm are supported by the bed mount, wherein no portion of the tubular base, the telescoping member, and the support arm contact the floor, and wherein the telescoping member rotates relative to the tubular base allowing the support arm to rotate relative to the bed mount about the axis of the tubular base.

9. The robotic system of claim 8, wherein the clearance height is maintained during operation of the robotic system.

10. The robotic system of claim 9, wherein a majority of the tubular base is arranged beneath the operating table surface of the surgical bed in a space disposed the operating table surface of the surgical bed and the floor.

11. The robotic system of claim 8, further comprising:
a surgical arm attached to the distal end of the support arm, wherein the surgical arm is attached at a revolute joint disposed between the support arm and the surgical arm, and wherein the surgical arm comprises a robotic mechanism having at least five degrees of freedom.

12. The robotic system of claim 8, further comprising:
a first degree of freedom between the bed mount and the telescoping member corresponding to a linear translational degree of freedom of the robotic system; and
a second degree of freedom between the support arm and the bed mount corresponding to a rotational degree of freedom of the robotic system,
wherein the robotic system comprises a total of two degrees of freedom between the bed mount and the support arm, the two degrees of freedom comprising only the first degree of freedom and the second degree of freedom.

13. The robotic system of claim 8, wherein the support arm comprises a prismatic joint that provides linear translation of the distal end of the support arm relative to the axis of the tubular base.

14. The robotic system of claim 8, wherein the telescoping member is rotationally fixed relative to the tubular base and a rotational degree of freedom is disposed between the support arm and the second end of the telescoping member allowing the support arm to rotate relative to the bed mount and the telescoping member about the axis of the tubular base.

15. The robotic system of claim 8, wherein at least one of the tubular base and the telescoping member is polygonal in cross-section, and wherein an axis of the telescoping member coincides with the axis of the tubular base.

16. A robotic system, comprising:
a bed mount bracket attached to a surgical bed adjacent an operating table surface of the surgical bed;
a column extending from an upper end of the column to a lower end of the column, the column fixedly attached to the bed mount bracket at the upper end of the column, wherein the upper end of the column is arranged adjacent the operating table surface of the surgical bed, wherein the lower end of the column is arranged beneath the operating table surface of the surgical bed and offset a clearance height from a floor, wherein the column comprises a telescoping member comprising a first end disposed inside the column between the operating table surface of the surgical bed and the floor, wherein the first end is configured to linearly translate along an axis of the column relative to the bed mount bracket in a space between the operating table surface of the surgical bed and the floor during operation of the robotic system, the column and telescoping member providing a first degree of freedom for the robotic system;
a support arm attached to the column, the support arm extending a length from a first point to a second point, the support arm disposed perpendicular to the column; and
a revolute joint disposed between the support arm and the bed mount bracket, the revolute joint configured to provide rotation of the support arm about the axis of the column, the revolute joint providing a second degree of freedom for the robotic system, and wherein the telescoping member rotates relative to the column allowing the support arm to rotate relative to the bed mount bracket about the axis of the column.

17. The robotic system of claim 16, wherein the revolute joint is disposed between the column and the support arm.

18. The robotic system of claim 16, wherein the robotic system comprises a total of two degrees of freedom between the bed mount bracket and the support arm, the two degrees of freedom comprising only the first degree of freedom and the second degree of freedom for the robotic system.

19. The robotic system of claim 16, wherein the clearance height is maintained during operation of the robotic system.

20. The robotic system of claim 16, wherein a majority of the column is arranged beneath the operating table surface of the surgical bed in a space disposed the operating table surface of the surgical bed and the floor.

* * * * *